United States Patent
Shiomi et al.

(10) Patent No.: US 7,363,226 B2
(45) Date of Patent: Apr. 22, 2008

(54) PSYCHOSOMATIC DIAGNOSIS SYSTEM

(75) Inventors: Kakuichi Shiomi, Tokyo (JP); Michiko Takaoka, 401, Metro Building, 5-11, Higashi-shimbashi 2-chome, Minato-ku, Tokyo 105-0021 (JP); Naritomo Meguro, Tokyo (JP); Nobuhiro Furuse, Tokyo (JP); Yoshio Sugimoto, Tokyo (JP)

(73) Assignees: Electronic Navigation Research Inst., Tokyo (JP); Kakuichi Shiomi, Tokyo (JP); Michiko Takaoka, Tokyo (JP); Mitsubishi Space Software Co., Ltd., Tokyo (JP)

( * ) Notice: Subject to any disclaimer, the term of this patent is extended or adjusted under 35 U.S.C. 154(b) by 756 days.

(21) Appl. No.: 10/493,749

(22) PCT Filed: Nov. 11, 2002

(86) PCT No.: PCT/JP02/11738

§ 371 (c)(1),
(2), (4) Date: Apr. 28, 2004

(87) PCT Pub. No.: WO2004/043259

PCT Pub. Date: May 27, 2004

(65) Prior Publication Data

US 2005/0102145 A1 May 12, 2005

(51) Int. Cl.
*G10L 15/22* (2006.01)
*A61B 5/12* (2006.01)

(52) U.S. Cl. .................... 704/270; 704/275; 706/924

(58) Field of Classification Search .............. 706/924; 600/300
See application file for complete search history.

(56) References Cited

U.S. PATENT DOCUMENTS

| | | | | |
|---|---|---|---|---|
| 5,935,060 A | * | 8/1999 | Iliff | 600/300 |
| 6,876,964 B1 | * | 4/2005 | Shiomi et al. | 704/202 |
| 7,124,075 B2 | * | 10/2006 | Terez | 704/203 |
| 2004/0107105 A1 | * | 6/2004 | Shomi et al. | 704/270 |
| 2004/0243401 A1 | * | 12/2004 | Shiomi et al. | 704/206 |
| 2005/0065412 A1 | * | 3/2005 | Shiomi et al. | 600/300 |
| 2005/0108014 A1 | * | 5/2005 | Shiomi et al. | 704/255 |
| 2006/0232430 A1 | * | 10/2006 | Takaoka et al. | 340/575 |
| 2006/0265444 A1 | * | 11/2006 | Shiomi et al. | 708/446 |
| 2007/0174377 A2 | * | 7/2007 | Shiomi et al. | 708/446 |

FOREIGN PATENT DOCUMENTS

| | | |
|---|---|---|
| JP | 4208136 | 7/1992 |
| JP | 7055226 | 3/1995 |
| JP | 2000-113347 | 4/2000 |

* cited by examiner

*Primary Examiner*—Martin Lerner
(74) *Attorney, Agent, or Firm*—Finnegan, Henderson, Farabow, Garrett & Dunner, L.L.P.

(57) ABSTRACT

A psychosomatic diagnosis system in which evaluation of the psychosomatic condition of a person to be diagnosed is performed automatically and objectively, based on the response by voice with respect to a question and the like asked to the person to be diagnosed. The system includes an index database, a speech processing section for obtaining voice as a speech signal, an analog to digital conversion section for converting the speech signal into a digital speech signal, a data processing section for calculating a human strange attractor by using the chaos theory and storing the human strange attractor in the index database, an attractor evaluation section for performing a quantitative evaluation by using the calculated human strange attractor, and a display section for displaying the evaluation result.

8 Claims, 7 Drawing Sheets

PSYCHOSOMATIC DIAGNOSIS SYSTEM

TECHNICAL FIELD

The present invention relates to a psychosomatic diagnosis system for diagnosing mind and body of a human being automatically and objectively. More specifically, the present invention relates to a psychosomatic diagnosis system in which evaluation of the psychosomatic condition of a person to be diagnosed is performed automatically and objectively, based on a verbal response with respect to questions and the like asked to the person to be diagnosed.

BACKGROUND ART

Conventionally, when the psychosomatic condition of a person to be diagnosed (hereinafter, referred to as a "subject") is evaluated, physiological conditions such as blood pressure, pulse, perspiration, reaction of the pupil and the like, and carbon dioxide concentration in expiration are measured. A person who gives diagnosis (hereinafter, referred to as a "diagnosing person") with respect to the subject asks appropriate detailed questions about the condition of the subject, based on the measurement results, and understands these based on his experience and knowledge, to evaluate the psychosomatic condition of the subject.

When the mind and body condition of the subject is evaluated, it is necessary to measure the physiological condition of the subject. However, at the time of measurement of the physiological condition, it is necessary to bring sensors required for the measurement into contact with the body of the subject or attach the sensors to the subject. Hence, the measurement is not handy, and also gives stress to the subject, thereby decreasing the reliability of the measurement result itself.

In order to prevent a decrease in the reliability, Japanese Patent No. 3151489 discloses apparatus for diagnosing tiredness or doziness of the subject by voice. In this invention, a change in the physiological condition (for example, the fatigue degree or doze) of the subject is captured by measurement of the obtained voice with the lapse of time.

In other words, in this invention, voice is obtained by the apparatus for detecting the fatigue degree or doze, and a Lyapunov index is calculated from the voice and compared with a Lyapunov index of the past condition such as tiredness or doziness of the subject, to thereby obtain the physiological condition of the subject.

However, when the objective evaluation with respect to the psychosomatic condition is calculated, the response of the subject with respect to questions and the like from the diagnosing person (that is, the voice uttered by the subject with respect to the questions and the like) becomes one of the important factors. However, it cannot be obtained in this invention. Moreover, the questions and the like asked to the subject should be appropriate corresponding to the subject, but it is not applicable to this invention. In other words, if the same thing is to be performed as in the present invention by using this invention, the diagnosing person should have sufficient experience, consider and ask appropriate questions based on the experience by himself.

The psychosomatic condition of the subject can be evaluated more accurately, not by simply asking questions and the like to the subject by the diagnosing person in an interview as before, but by giving the subject the false impression that he/she is under some circumstances, to intentionally put the subject in circumstances (for example, relaxed situation, or situation under tension or stress) desired by the diagnosing person and observing the reaction of the subject (voice of the subject with respect to the questions). But it is also not applicable to this invention. That is, the diagnosing person cannot control the situation of the subject.

DISCLOSURE OF THE INVENTION

In view of the above situation, the present inventor has invented a psychosomatic diagnosis system that makes it possible to eliminate subjectivity of the diagnosing person and to objectively determine the psychosomatic condition of the subject by utterance with respect to questions and the like. Appropriate questions are provided based on the information of the subject stored in advance, and as a result, the diagnosing person does not have to have abundant experiences as before.

In the present invention, not only the voice of the subject with respect to the questions and the like by the diagnosing person is obtained, but also it is possible to put the subject in the situation desired by the diagnosing person (that is, to give the subject a virtual sense of reality to intentionally change the situation of the subject). As a result, the psychosomatic condition of the subject can be evaluated more accurately than the simple evaluation based on the voice.

The invention according to claim 1 is a psychosomatic diagnosis system for diagnosing the psychosomatic condition by voice uttered by a person to be diagnosed psychosomatically with respect to questions and the like, comprising: index database in which evaluation results and information for identifying the person to be diagnosed are stored in association with each other; a speech processing section that obtains voice uttered by the person to be diagnosed with respect to the questions and the like as a speech signal; an analog to digital conversion section that converts the speech signal to a digital speech signal by digitization; a data processing section that calculates a human strange attractor from the digital speech signal by using the chaos theory, and stores the calculated human strange attractor in the index database; an attractor evaluation section that performs quantitative evaluation based on the calculated human strange attractor and the past human strange attractor of the person to be diagnosed or another person to be diagnosed stored in the index database; and a display section that displays the evaluation result.

Objective diagnosis can be provided by obtaining voice uttered by the subject (the subject (the person to be diagnosed psychosomatically) includes a person who is diagnosed unconsciously (for example, the person's voice is observed from another room and diagnosed) as well as a person who is diagnosed consciously) with respect to the questions and the like asked by the diagnosing person, and analyzing the voice according to the chaos theory. Further, since the diagnosis is provided from the voice, it is not necessary to attach sensors to the subject, and hence the reliability of the diagnosis is improved without giving excessive stress to the subject.

At this time, the human strange attractor, which becomes the basis for diagnosis, is calculated by electronically processing the speech signal issued from the subject according to a predetermined procedure, to give quantitative evaluation using the calculation result. Therefore, the process leaves no room for subjectivity, and eliminates conventional judgment relying on the experience and subjectivity such as the sense of the diagnosing person, thereby providing objective evaluation result. The human strange attractor refers to phase space mapping information and an index such as the Lyapunov index.

Questions here are not limited to medical questions, and include non-medical questions and interviews, and also include a case where the diagnosing person directly asks questions to the subject, and a case where the psychosomatic diagnosis system according to the present invention provides the same feeling and interpretation as those obtained when the diagnosing person asks questions to the subject, through the sense of sight, sense of hearing, and sense of touch (for example, when a virtual sense of reality is provided by using a display of sentences, images, or projections having a relation with the questions provided to the subject by the diagnosing person, by which the content of the question can be imaged, or human voice, environmental noise, or effective sound).

In the present invention, the psychosomatic condition refers to a psychosomatic condition such as getting excited easily, including the person's natural character, potential character, character obtained by experience, occasional excited state, or diagnosis of manic-depressive, condition of losing self-confidence or likely losing self-confidence, the inner workings of a human mind to tell a lie or be going to tell a lie, or more simply, a tired state or an absent-minded state of being absorbed in other things.

An invention according to claim 2 is a psychosomatic diagnosis system comprising: subject database for storing information of the person to be diagnosed; and a question supply section that supplies at least one question to a diagnosing person, based on the information of the person to be diagnosed stored in the subject database.

In the present invention, when the diagnosing person diagnoses the subject, questions and the like are provided based on the subject's information. As a result, the diagnosing person does not require experience, and even a person who does not have abundant experiences (or automatically) can easily diagnose the mind and body of the subject.

An invention according to claim 3 is a psychosomatic diagnosis system having a visual simulation display section that gives an effect of visual simulation and/or an aural simulation speaker section that gives an effect of aural simulation and/or a tactile simulation operation section that gives an effect of tactile simulation, with respect to the person to be diagnosed.

A delicate change occurs in the subject, when the subject understands that he/she is going to be diagnosed. Therefore, this change may give some influence to the evaluation result, but it has been heretofore difficult to eliminate this influence. In the present invention, by giving an effect of simulation, which directly acts on the sense of vision, the sense of hearing, or the sense of touch of the subject, the subject can be placed under a relaxed situation or an optimum situation appropriate to the diagnosis purpose (situation desired by the diagnosing person), thereby enabling a more accurate evaluation.

An invention according to claim 4 is a psychosomatic diagnosis system, wherein the speech processing section has a preamplifier that performs preprocessing of the speech signal before conversion of the speech signal into a digital speech signal in the analog to digital conversion section, and an audio filter.

In the present invention, when the subject uses a microphone, the speech signal is sampling-processed, thereby enabling extraction of amore accurate speech signal, which leads to improvement of evaluation accuracy. The microphone may be any known device for obtaining voice, and includes a bone conduction microphone.

An invention according to claim 5 is a psychosomatic diagnosis system for diagnosing the psychosomatic condition by voice uttered by a person to be diagnosed psychosomatically with respect to questions and the like, comprising: index database in which evaluation results and information for identifying the person to be diagnosed are stored in association with each other; a speech processing section that obtains voice of the person to be diagnosed with respect to the questions and the like stored on a recording medium as a speech signal; an analog to digital conversion section that obtains the speech recorded on the recording medium as a speech signal, or converts the speech signal obtained in the speech processing section to a digital speech signal by digitization; a data processing section that calculates a human strange attractor from the digital speech signal recorded on the recording medium or received from the analog to digital conversion section, by using the chaos theory, and stores the calculated human strange attractor in the index database; an attractor evaluation section that gives a quantitative evaluation based on the calculated human strange attractor and the past human strange attractor of the person to be diagnosed or another person to be diagnosed stored in the index database; and a display section that displays the evaluation result.

The response to the questions provided by the diagnosing person is stored on the recording medium, and the speech signal is electronically processed according to a predetermined procedure based on the voice recorded on the recording medium, thereby to calculate a human strange attractor, which becomes the basis for diagnosis, and to provide a quantitative evaluation using the calculation result. Therefore, the process leaves no room for subjectivity of the diagnosing person, and eliminates conventional judgment relying on the experience and subjectivity such as the sense of the diagnosing person, thereby providing objective evaluation result.

Moreover, evaluation of the subject becomes possible by using voice recorded on a recording medium such as a tape recorder or an IC memory in advance, not by receiving a speech input from the microphone or the like. As a result, ex-post evaluation of the subject becomes possible, and for example, when the schedules of the subject and the diagnosing person do not agree, the response of the subject with respect to the questions provided in advance by a person other than the diagnosing person is recorded on a recording medium, and the diagnosing person can make judgment later, based on the recorded voice.

An invention according to claim 6 is a psychosomatic diagnosis system for diagnosing the psychosomatic condition by voice uttered by a person to be diagnosed psychosomatically with respect to questions and the like, comprising: index database in which evaluation results and information for identifying the person to be diagnosed are stored in association with each other; a speech processing section that obtains voice of the person to be diagnosed with respect to the questions and the like as a speech signal via a network; an analog to digital conversion section that converts the speech signal to a digital speech signal by digitization; a data processing section that calculates a human strange attractor from the digital speech signal by using the chaos theory, and stores the calculated human strange attractor in the index database; an attractor evaluation section that gives a quantitative evaluation based on the calculated human strange attractor and the past human strange attractor of the person to be diagnosed or another person to be diagnosed stored in the index database; and a display section that displays the evaluation result. When the speech signal is an analog speech signal, the speech signal is received by the speech processing section or the analog to digital conversion section, and when the speech signal is a digital speech signal, the digital speech signal is received by the data processing section.

According to the present invention, the psychosomatic diagnosis system enables transfer of voice via the network with a subject who lives in a remote area, by using a telephone, a computer or the like. As a result, the subject does not have to go to a place where the psychosomatic diagnosis system is installed, and can use the psychosomatic diagnosis system without traveling.

When a telephone line or the like is used as the network, since the speech signal is an analog signal, the analog signal is digitized to enable digital processing thereafter. When the Internet or the like is used as the network, since the speech signal is a digital signal, useless process can be omitted by calculating the human strange attractor directly from the signal, thereby enabling high-speed processing.

An invention according to claim 7 is a psychosomatic diagnosis system for diagnosing the psychosomatic condition by voice uttered by a person to be diagnosed psychosomatically with respect to questions and the like, comprising: index database in which evaluation results and information for identifying the person to be diagnosed are stored in association with each other; a processing function distribution section that transmits to a subject's terminal held by the person to be diagnosed a speech processing section for obtaining the voice of the person to be diagnosed as a speech signal, an analog to digital conversion section for converting the speech signal to a digital speech signal by digitization, a questioning section for providing the questions and the like to the person to be diagnosed, a data processing section for calculating a human strange attractor from the digital speech signal by using the chaos theory, and transmitting the calculation result to the psychosomatic diagnosis system, and a display section for receiving and displaying the questions and the evaluation in the attractor evaluation section; an attractor evaluation section that stores the human strange attractor calculated on the subject's terminal in the index database and gives a quantitative evaluation based on the calculated human strange attractor and the past human strange attractor of the person to be diagnosed or another person to be diagnosed stored in the index database; and a data reception and distribution section that transmits the questions and the like in the question supply section to the subject's terminal, receives the calculation result from the subject's terminal, and transmits the evaluation result obtained in the attractor evaluation section to the subject's terminal.

According to the present invention, the processing functions can be distributed by using a browser or the like used for the Internet, which has become widespread recently. In other words, processing from the speech processing to the calculation of the human strange attractor is performed by the subject's terminal, and only the result thereof is received by the psychosomatic diagnosis system, to evaluate it. As a result, load distribution becomes possible, thereby enabling high-speed processing.

Further, when the subject is to be diagnosed, optimum question can be provided to the subject, while eliminating the subjectivity of the diagnosing person, by providing the questions and the like from the system. Furthermore, by automatically providing questions based on the information relating to the subject and evaluating the response based on the past statistics of the psychosomatic diagnosis system, the diagnosing person himself is not always necessary, and the subject alone can obtain and read the result.

An invention according to claim 8 is a psychosomatic diagnosis system comprising subject database for storing the information relating to the person to be diagnosed, and a question supply section that supplies at least one question to the diagnosing person, based on the information of the person to be diagnosed, stored in the subject database.

According to the present invention, since questions and the like are supplied based on the information of the subject, the diagnosing person does not require experience, and even a person who does not have abundant experiences (or automatically) can easily diagnose the mind and body of the subject.

In the inventions according to claims 1 to 8, the diagnosing person can basically give diagnosis without contacting with the subject, thereby enabling a highly reliable and simple psychosomatic diagnosis system, without providing a stress due to the diagnosis with respect to the subject.

Particularly, diagnosis can be automatically provided from the subject's voice obtained by a general microphone, and the subject's psychosomatic condition can be properly and easily evaluated by any user of the system, without requiring high level skills with respect to the operation of the psychosomatic diagnosis system itself or experience of analysis or the like of the mental status. As a result, the subject can evaluate the psychosomatic condition without requiring a diagnosing person, who is a specialist.

Furthermore, since diagnosis from the voice becomes possible, diagnosis from voice transmitted through a phone or a network such as Internet, and voice recorded by a tape recorder or the like becomes also possible, thereby enabling correspondence in a wide range of operation mode.

BRIEF DESCRIPTION OF DRAWINGS

FIG. 3 is a system block diagram indicating one example of the system configuration of speech input using a microphone or the like.

BEST MODE FOR CARRYING OUT THE INVENTION

Figure 1:
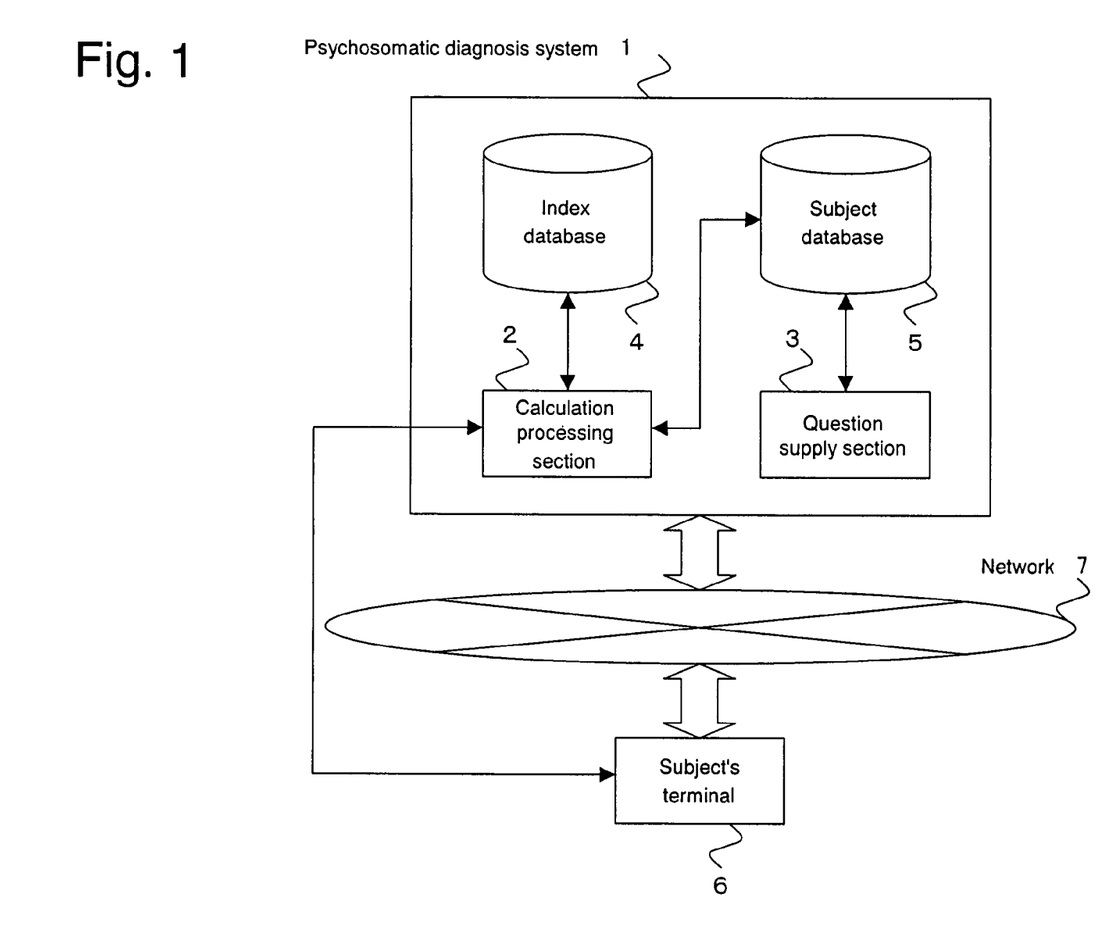
FIG. 1 is a system block diagram indicating one example of the system configuration according to the present invention.

One example of the embodiments of the present invention will be described in detail, with reference to the drawings. FIG. 1 is a system block diagram indicating one example of the system configuration according to the present invention. A psychosomatic diagnosis system 1 has a calculation processing section 2, a question supply section 3, index database 4, and subject database 5, and can transfer data (speech signal, evaluation data and the like) between the psychosomatic diagnosis system 1 and a subject's terminal 6 by which the subject inputs voice.

The network 7 may be any of a telephone network, an open network such as Internet, and a closed network such as LAN, and may be wired or wireless.

The subject's terminal 6 refers to a terminal by which the subject inputs voice, and may be a microphone, a phone, a mobile phone, a personal handy phone, a PDA, or a personal computer.

Figure 2:
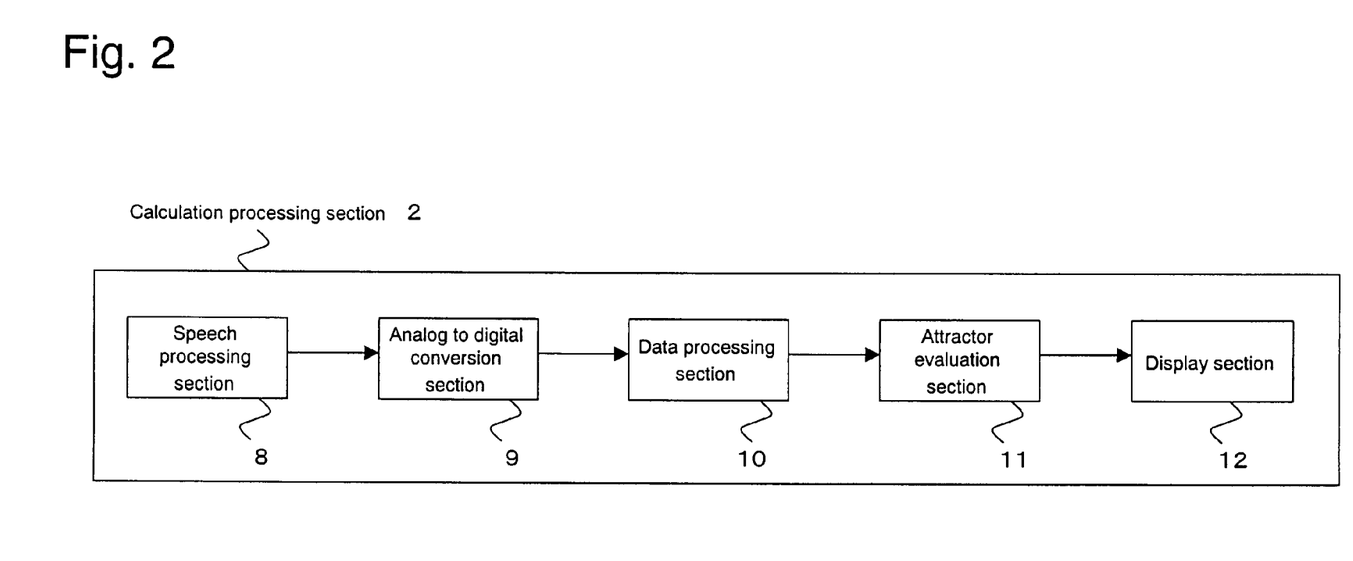
FIG. 2 is a system block diagram indicating one example of the system configuration of a calculation processing section in the present invention.

The calculation processing section 2 is a unit which performs analysis according to the chaos theory based on the input voice, to calculate a human strange attractor (phase space mapping information and an index such an Lyapunov index). The calculation processing section 2 has a speech processing section 8, an analog to digital conversion section 9, a data processing section 10, an attractor evaluation section 11, and a display section 12. FIG. 2 illustrates a system block diagram, being one example of the system configuration of the calculation processing section 2. In the data processing section 10 and the attractor evaluation section 11, processing by hardware or processing by software may be performed.

The speech processing section 8 is a unit which performs proper adjustment of the sampling period and adjustment of a signal amplification level with respect to the speech signal input from hardware capable of reproducing and outputting speech, such as the subject's terminal 6, a magnetic tape recorder, and a magnetic disk.

The analog to digital conversion section 9 is a unit which converts an analog speech signal sampled by the speech processing section 8 into a digital speech signal.

The data processing section 10 is a unit which analyzes time series data in the digital speech signal based on a known method according to the chaos theory to calculate a human strange attractor.

The attractor evaluation section 11 is a unit which performs known quantitative evaluation such as change detection or statistical analysis, by using the human strange attractor calculated in the data processing section 10, and the past human strange attractor of the subject or another subject, stored in the index database 4 (described later).

The display section 12 is a unit which displays the result of evaluation performed in the attractor evaluation section 11 by using a numerical value, a graph or the like, so that the diagnosing person (or the subject according to circumstances) can read the evaluation result.

The question supply section 3 is a unit which selects a question and the like to be provided to the subject from the diagnosing person, based on the information relating to the subject stored in the subject database 5. In this case, the diagnosing person may select a question from the question list, or an optimum question may be automatically selected based on the information relating to the subject.

The index database 4 is database for storing the human strange attractor calculated in the calculation processing section 2 in association with the information for identifying the subject (hereinafter referred to as "subject discrimination code").

The subject database 5 is database for storing the subject's information, for example, living environment, worries, the present situation, hobbies and preferences.

Figure 3:
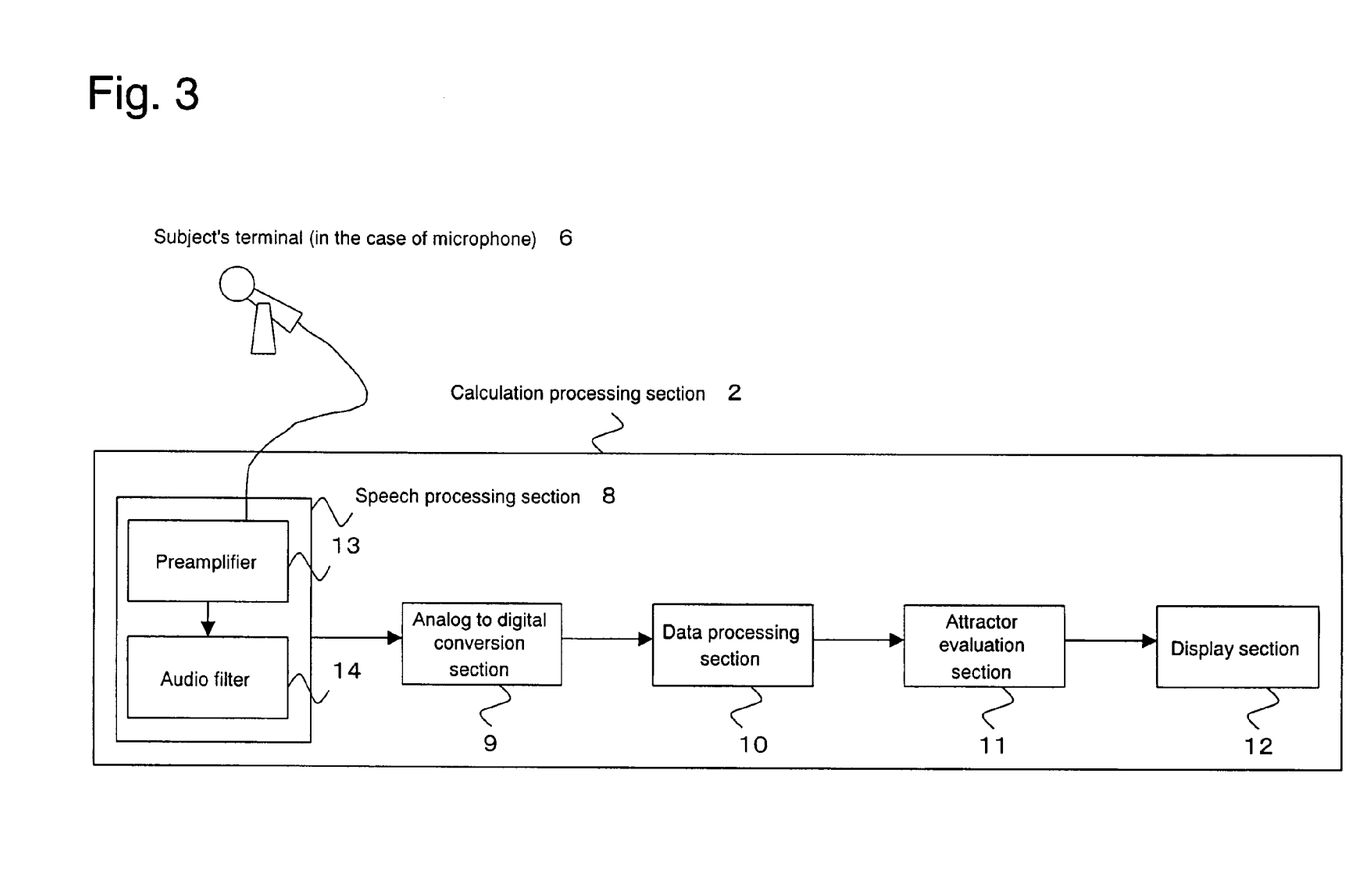

One example of the process flow according to the present invention will be described in detail. At first, one example of the process flow is shown, in which the subject's terminal 6 is a microphone or a bone conduction microphone, and is directly connected to the psychosomatic diagnosis system 1, and the subject inputs the response with respect to the questions from the diagnosing person by voice. The conceptual diagram of the system configuration of the psychosomatic diagnosis system 1 in this case is shown in FIG. 3.

The diagnosing person reads the information of the subject stored in the subject database 5 via the question supply section 3, and selects a question or the like from the question supply section 3 (or the question supply section 3 automatically selects a question or the like based on the information relating to the subject stored in the subject database 5), to ask the question to the subject. When the subject himself utters words, this process is not always necessary.

From the response by voice with respect to the question by the diagnosing person, the voice is input via the microphone or the bone conduction microphone in the subject's terminal 6 to become a speech signal. The input speech signal is input from the subject's terminal 6 to an audio filter 14 via a preamplifier 13, subjected to proper adjustment of sampling period and adjustment of the signal amplification level, and input to the analog to digital conversion section 9.

The analog to digital conversion section 9 converts the speech signal sampled by the speech processing section 8 into a digital speech signal, and inputs the digital speech signal to the data processing section 10. The data processing section 10 having received the digital speech signal analyzes the time series data in the digital speech signal by using the known method according to the chaos theory, to calculate the human strange attractor. The data processing section 10 stores the calculated human strange attractor together with the subject discrimination code in the index database 4.

After the human strange attractor is calculated in the data processing section 10, the attractor evaluation section 11 extracts the past human strange attractor of the subject and/or another subject stored in the index database 4, and the extracted human strange attractor and the calculated human strange attractor are used to perform quantitative evaluation such as change detection and statistical analysis, and displays the result to the diagnosing person (the subject according to circumstances), by using a numerical value, a graph or the like. The diagnosing person (the subject according to circumstances) can read this, to understand the evaluation of the objective psychosomatic condition of the subject.

Figure 4:
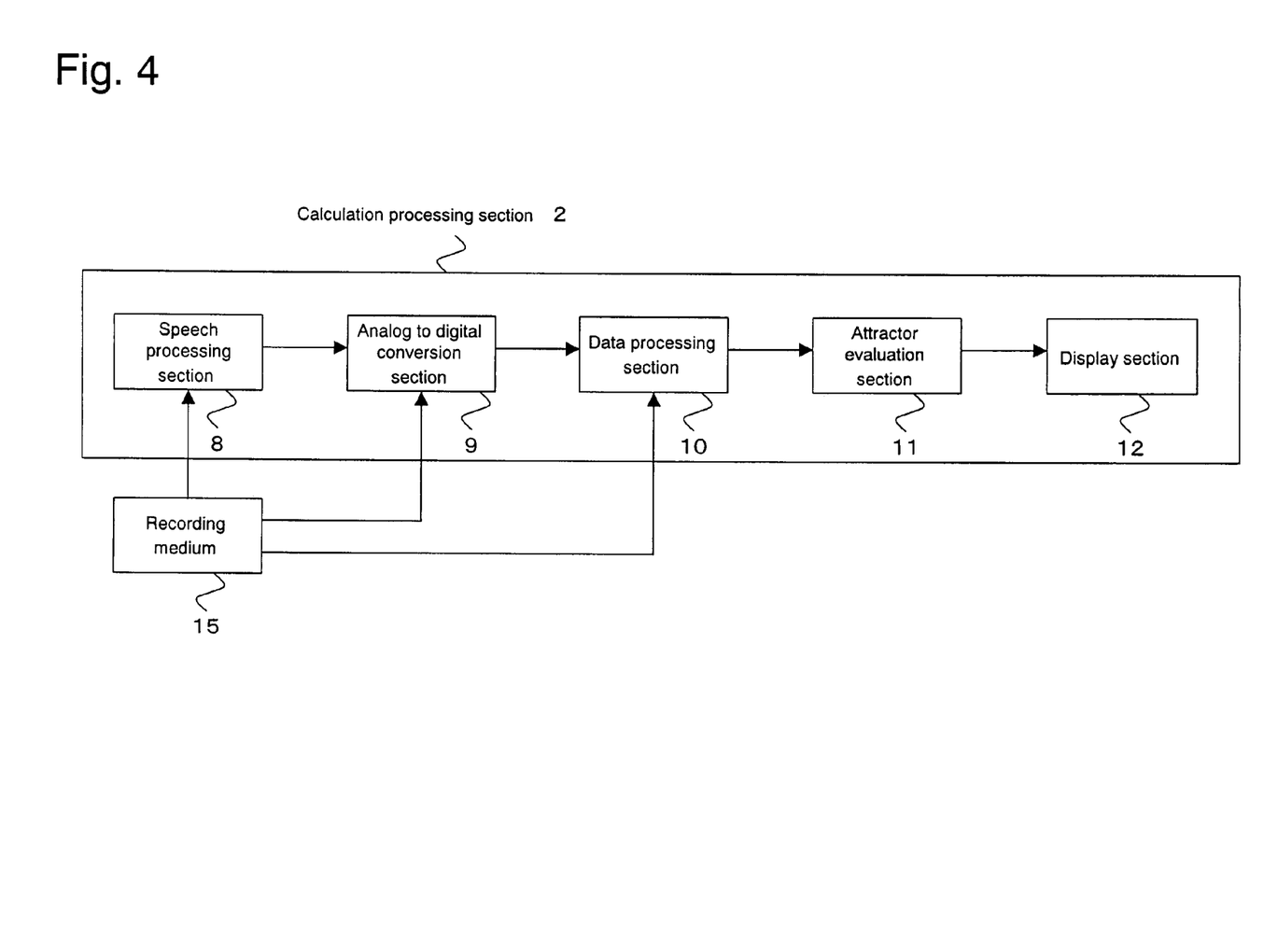
FIG. 4 is a system block diagram indicating one example of the system configuration of speech input using a recording medium.

One example of the process flow when the response by voice of the subject with respect to the question provided by the diagnosing person is recorded on a recording medium 15 such as a magnetic tape, a magnetic disk or an IC memory, and a speech signal is input from the recording medium 15 to the speech processing section 8 will be described next. The conceptual diagram of the system configuration of the psychosomatic diagnosis system 1 in this case is shown in FIG. 4.

The recording method on the recording medium 15 includes a case in which the speech signal is input as an analog signal, and a case in which the speech signal is input as a digital signal. When the speech signal is an analog signal (for example, when speech is recorded on a tape recorder), the speech signal is input to the speech processing section 8 or the analog to digital conversion section 9, to convert the analog signal into a digital speech signal.

On the other hand, when the speech signal is a digital speech signal on the recording medium 15 (for example, when speech is recorded on an IC memory), or after the analog signal is converted into a digital speech signal in the analog to digital conversion section 9, the digital speech signal is input to the data processing section 10. The process thereafter is the same as in the first example, thereby enabling understanding of the evaluation of the objective psychosomatic condition of the subject.

Figure 5:
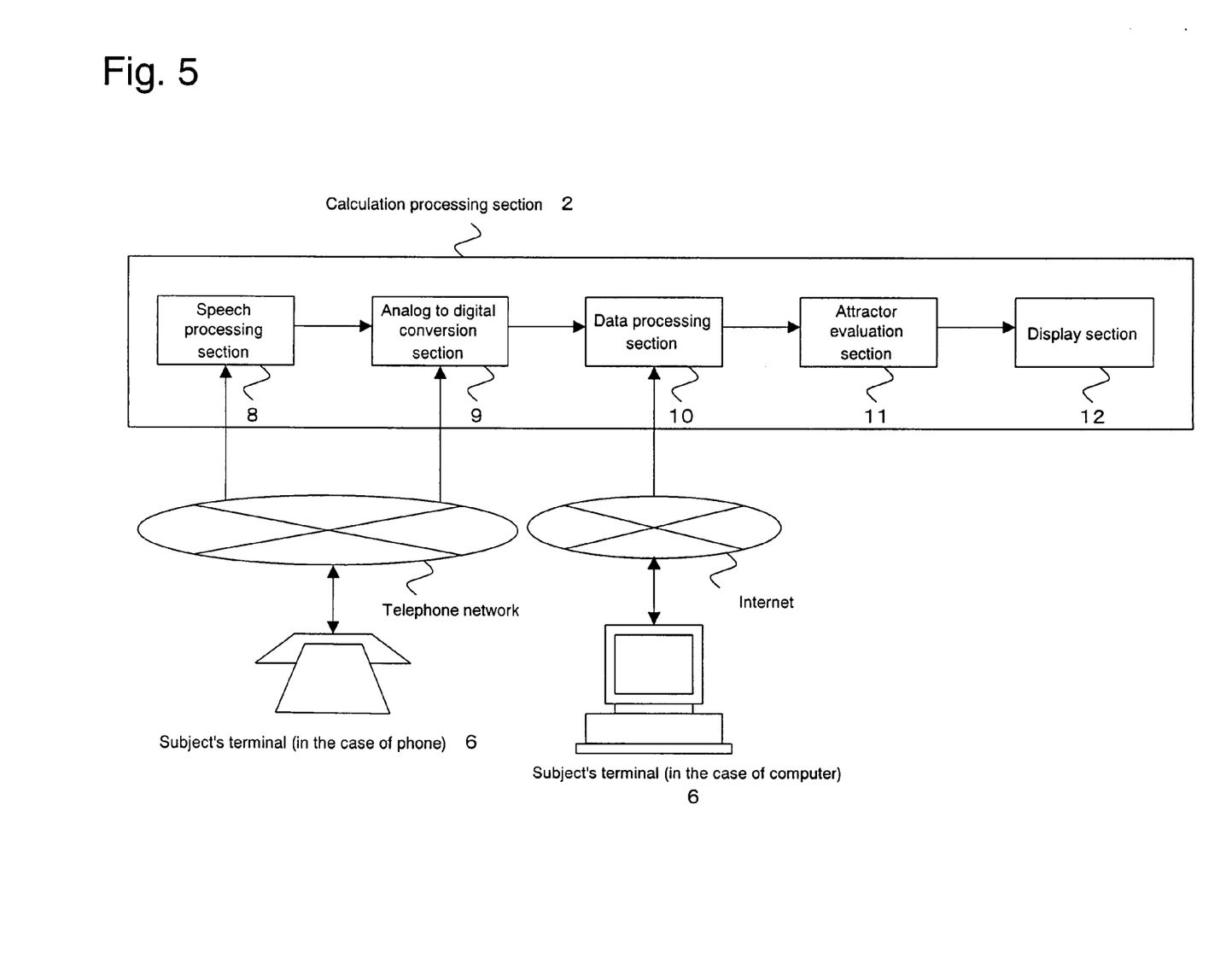
FIG. 5 is a system block diagram indicating one example of the system configuration of speech input via a network.

Next, explanation is given to a case where the psychosomatic diagnosis system 1 transfers the speech signal between the subject's terminal 6 and the psychosomatic diagnosis system 1 via the network 7, to evaluate the objective psychosomatic condition of the subject. The conceptual diagram of the system configuration of the psychosomatic diagnosis system 1 in this case is shown in FIG. 5.

When the subject's terminal 6 transmits an analog signal, for example from a phone, to the psychosomatic diagnosis system 1 as a speech signal, the subject speaks via the phone or the like, so that the speech signal, being the analog signal, is transmitted from the subject's terminal 6 to the speech processing section 8. The speech processing section 8 receives the analog signal, and the analog signal is input from the preamplifier 13 to the audio filter 14, subjected to proper adjustment of sampling period and adjustment of the signal amplification level, and input to the analog to digital conversion section 9.

The analog to digital conversion section 9 converts the speech signal sampled by the speech processing section 8 into a digital speech signal, and inputs the digital speech signal to the data processing section 10.

On the other hand, when the speech signal is a digital speech signal through an interface between computers transmitted via the Internet or the like, the digital speech signal is directly input from the subject's terminal 6 to the data processing section 10. The processing thereafter is the same as in the first embodiment, thereby enabling understanding of the evaluation of the objective psychosomatic condition of the subject.

Figure 6:
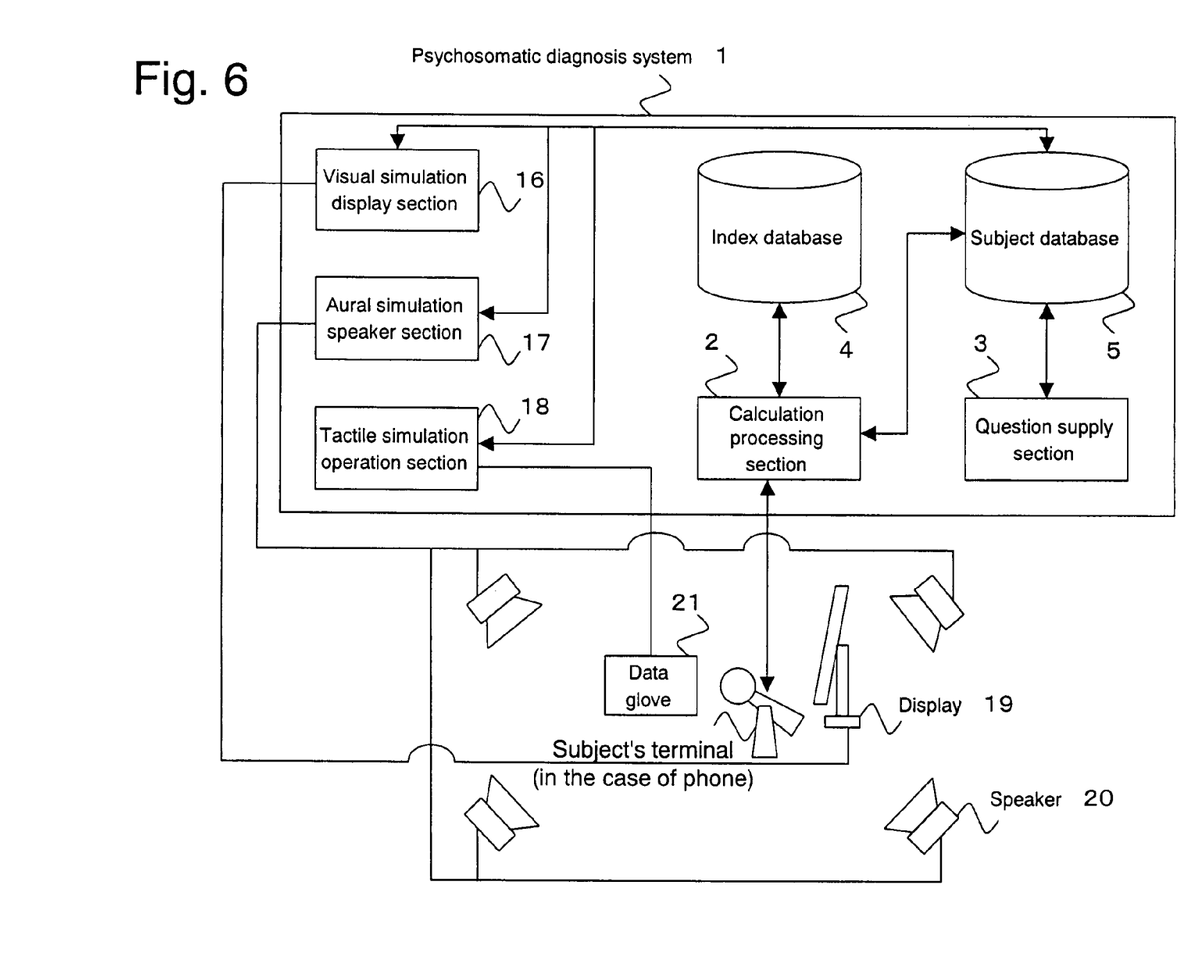
FIG. 6 is a system block diagram indicating one example of the system configuration in which a virtual sense of reality is provided to a subject to perform speech input.

This embodiment indicates a case where a function of providing a diagnosis environment closer to the actual environment with respect to the subject is added to the system configuration in Example 1, and explanation is given to an example of the psychosomatic diagnosis system 1, in which a visual simulation display section 16 is connected to an aural simulation speaker section 17 and a tactile simulation operation section 18, to provide the subject relaxed or optimum virtual sense of reality according to the diagnosis purpose. One example of the system configuration of the psychosomatic diagnosis system 1 in this case is shown in FIG. 6. The visual simulation display section 16 indicates a function of allowing a display 19 for displaying a stereoscopic image or the like to display the stereoscopic image, the aural simulation speaker section 17 indicates a function of allowing a speaker 20 which can output voice in the three-dimensional space to output the voice in the three-dimensional space, and the tactile simulation operation section 18 indicates a function of controlling a data glove 21 which gives feeling of touch, weight and the like with respect to the subject, to give sense of touch to the subject.

The diagnosing person extracts information of the subject in the subject database 5 via the question supply section 3, and provides the subject visual, aural, and tactile effects such that the subject can obtain a relaxed visual sense of reality, from the display 19, the speaker 20, and the data glove 21, via the visual simulation display section 16, the aural simulation speaker section 17, and the tactile simulation operation section 18. For example, when the subject likes hiking, the visual simulation display section 16 shows three-dimensional vision in the forest to the subject as a visual effect via the display 19, the aural simulation speaker section 17 generates three-dimensional sound such as a birdsong and waving sound of trees in the wind as an aural effect, and the tactile simulation operation section 18 provides a sense of touch of trees with respect to the subject via the data glove 21, thereby to give a sensation that the subject is in the forest, and a virtual sense of reality with respect to the subject.

Under such environment, the diagnosing person reads the subject's information stored in the subject database 5 via the question supply section 3, and selects a question or the like from the question supply section 3 (or the question supply section 3 automatically selects a question or the like based on the information relating to the subject stored in the subject database 5), to ask the question to the subject.

As a result, the environment of the subject can be controlled from point to point according to the situation of the subject, so that the subject can be placed under various environments, thereby enabling understanding of accurate reaction of the subject.

The subject answers the question from the diagnosing person, and the voice becomes a speech signal via the microphone or the bone conduction microphone in the speech processing section 8. The process flow thereafter is the same as in the first embodiment, and hence the explanation thereof is omitted. As a result, the evaluation of the objective psychosomatic condition of the subject under the environment corresponding to the diagnosis purpose can be comprehended.

Figure 7:
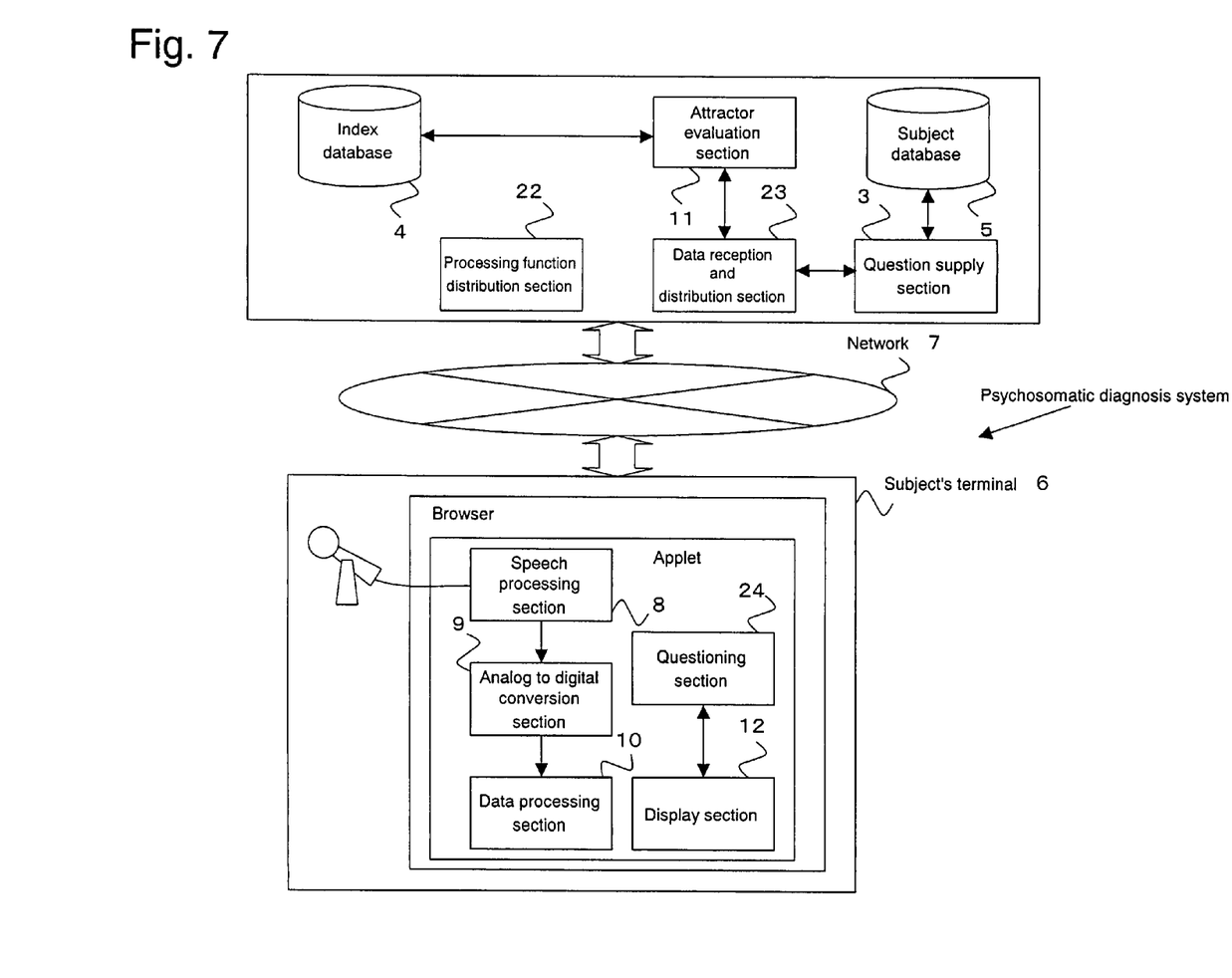
FIG. 7 is a system block diagram indicating one example of the system configuration when the functions are distributed.

One example of a process flow when the psychosomatic diagnosis system 1 is not performed on one terminal, but the functions thereof are distributed will be described below. One example of the system configuration of the psychosomatic diagnosis system 1 in this case is shown in FIG. 7. In this case, a computer having a browser and the like, a mobile phone, a personal handy phone, a PDA or the like is preferable as the subject's terminal 6.

The psychosomatic diagnosis system 1 has a processing function distribution section 22, an attractor evaluation section 11, a data reception and distribution section 23, the question supply section 3, the index database 4, and the subject database 5, and is capable of transfer of data between the psychosomatic diagnosis system 1 and the subject's terminal 6 via the network 7. Needless to say, the subject's terminal 6 is capable of operating the application software such as applet on the browser, and equipped with a microphone or the like. In this embodiment, an example in which various functions are handled by software by using the applet will be described, but needless to say, other methods may be used.

The processing function distribution section 22 is a unit that transmits the processing functions of the speech processing section 8 for sampling an analog signal, the analog to digital conversion section 9 for converting the analog signal into a digital speech signal, the data processing section 10 for calculating the human strange attractor and transmitting the calculation result to the attractor evaluation section 11 in the psychosomatic diagnosis system 1, a questioning section 24 for receiving a question with respect to the subject from the data reception and distribution section 23 via the network 7 to provide it to the subject via the display section 12, and the display section 12 for receiving the question and the evaluation result from the psychosomatic diagnosis system 1 and displaying these by using a numerical value, a graph or the like, as the applet from the psychosomatic diagnosis system 1 to the subject's terminal 6 via the network 7.

The attractor evaluation section 11 is a unit that stores the human strange attractor received via the data reception and distribution section 23 (described below) in the index database 4, perform quantitative evaluation based on the received human strange attractor and the past human strange attractor of the subject or another subject, and distributes the evaluation result via the data reception and distribution section 23.

The data reception and distribution section 23 is a unit that receives the human strange attractor from the subject's terminal 6 to input it to the attractor evaluation section 11, and distributes the evaluation result obtained in the attractor evaluation section 11 to the subject's terminal 6 via the network 7. Further, the data reception and distribution section 23 transmits questions and the like supplied from the question supply section 3 to the subject.

The question supply section 3 is a unit that extracts the information relating to the subject from the subject database 5, and transmits at least one question with respect to the relevant subject via the data reception and distribution section 23.

The questioning section 24 is a unit that allows the display section 12 to display the question transmitted from the data reception and distribution section 23 via the network 7 to thereby ask the question to the subject. The subject answers the question by voice.

One example of the process flow will be described below. The subject who desires to evaluate his/her psychosomatic condition accesses the psychosomatic diagnosis system 1 from the browser on the subject's terminal 6 via the network 7, and receives the applet from the processing function distribution section 22 in the psychosomatic diagnosis system 1.

The question supply section 3 in the psychosomatic diagnosis system 1 creates at least one question based on the information relating to the subject stored in the subject database 5, and transmits the question to the subject's terminal 6 via the data reception and distribution section 23.

When the questioning section 6[24] in the subject's terminal 6 receives the question, the questioning section 6[24] displays the question via the display section 12, and asks the question to the subject. The subject having received this question inputs the response by voice.

The speech processing section 8 having received the voice input via the microphone or the like performs proper adjustment of the sampling period and adjustment of the signal amplification level with respect to the speech signal, and inputs the speech signal to the analog to digital conversion section 9.

The analog to digital conversion section 9 converts the speech signal sampled by the speech processing section 8 into a digital speech signal, and inputs the digital speech signal to the data processing section 10. The data processing section 10 having received the digital speech signal analyzes the time series data in the digital speech signal, using a method according to the chaos theory, to calculate the human strange attractor.

The data processing section 10 transmits the calculated human strange attractor to the psychosomatic diagnosis system 1 via the network 7. Upon reception of the human strange attractor, the data reception and distribution section 23 in the psychosomatic diagnosis system 1 inputs the human strange attractor to the attractor evaluation section 11.

The attractor evaluation section 11 stores the human strange attractor in the index database 4, compares the received human strange attractor with the past human strange attractor of the subject or another subject, to perform quantitative evaluation such as change detection or statistical analysis, and distributes the evaluation result to the subject's terminal 6 via the data reception and distribution section 23.

Upon reception of the evaluation result, the display section 12 in the subject's terminal 6 displays the evaluation result with respect to the subject via the browser, by using a numerical value, a graph or the like. Whereby, the subject can understand the objective evaluation of the psychosomatic condition of himself/herself.

The respective units and database in the present invention are only logically divided by function, and may form the same area physically or virtually.

Needless to say, at the time of executing the present invention, a recording medium, on which the program of the software for realizing the functions in the embodiment is recorded, is supplied to the system, and the computer in the system reads out and executes the program stored on the recording medium to realize the present invention.

In this case, the program itself read out from the recording medium realizes the functions in the embodiment, and hence, the recording medium storing the program naturally constitutes the present invention.

As the recording medium for supplying the program, for example, a floppy disk, a hard disk, an optical disk, a magneto-optical disk, a non-volatile memory card and the like can be used.

Needless to say, the functions in the embodiment are realized not only by the computer which executes the read program, but also by the operating system operating on the computer which performs a part of or all of the actual processing based on the instruction of the program.

Moreover, after the program read from the recording medium is written on a non-volatile or volatile storage means provided in a function enhancement board inserted in the computer or a function enhancement unit connected to the computer, the function enhancement board or a processor equipped in the function enhancement unit may perform a part of or all of the actual processing based on the instruction of the program, to thereby realize the functions in the embodiment.

INDUSTRIAL APPLICABILITY

According to the present invention, the psychosomatic condition of the subject can be objectively determined based on the voice of the subject with respect to a question and the like, by eliminating the subjectivity of the diagnosing person. The question and the like can be appropriately provided based on the information of the subject stored in advance, and hence the diagnosing person does not have to have abundant experiences as before.

Further in the present invention, not only the voice of the subject with respect to the questions by the diagnosing person is obtained, but also it is possible to place the subject in the situation desired by the diagnosing person (that is, to give the subject a virtual sense of reality to intentionally change the situation of the subject). As a result, the psychosomatic condition of the subject can be evaluated more accurately than the simple evaluation based on the voice.

Furthermore, by distributing these functions via the network, even a subject in a remote area can obtain objective evaluation of the psychosomatic condition without requiring the diagnosing person.

The invention claimed is:

1. A psychosomatic diagnosis system for diagnosing the psychosomatic condition by voice uttered by a person to be diagnosed psychosomatically with respect to questions, comprising:
    an index database in which evaluation results and information for identifying the person to be diagnosed are stored in association with each other;
    a speech processing section that obtains voice uttered by the person to be diagnosed with respect to the questions as a speech signal;
    an analog to digital conversion section that converts the speech signal to a digital speech signal by digitization;
    a data processing section that calculates a human strange attractor from the digital speech signal by using the chaos theory, and stores the calculated human strange attractor in the index database;
    an attractor evaluation section that performs quantitative evaluation based on the calculated human strange attractor and the past human strange attractor of the person to be diagnosed or another person to be diagnosed stored in the index database; and
    a display section that displays the evaluation result.

2. A psychosomatic diagnosis system according to claim 1, comprising:
    subject database for storing information of the person to be diagnosed; and
    a question supply section that supplies at least one question to a diagnosing person, based on the information of the person to be diagnosed stored in the subject database.

3. A psychosomatic diagnosis system according to either one of claims 1 and 2, having a visual simulation display section that gives an effect of visual simulation and/or an aural simulation speaker section that gives an effect of aural simulation and/or a tactile simulation operation section that gives an effect of tactile simulation, with respect to the person to be diagnosed.

4. A psychosomatic diagnosis system according to claim 1, wherein the speech processing section has a preamplifier that performs preprocessing of the speech signal before conversion of the speech signal into a digital speech signal in the analog to digital conversion section, and an audio filter.

5. A psychosomatic diagnosis system for diagnosing the psychosomatic condition by voice uttered by a person to be diagnosed psychosomatically with respect to questions, comprising:
    an index database in which evaluation results and information for identifying the person to be diagnosed are stored in association with each other;
    a speech processing section that obtains voice of the person to be diagnosed with respect to the questions stored on a recording medium as a speech signal;
    an analog to digital conversion section that obtains the speech recorded on the recording medium as a speech signal, or converts the speech signal obtained in the speech processing section to a digital speech signal by digitization;
    a data processing section that calculates a human strange attractor from the digital speech signal recorded on the recording medium or received from the analog to digital conversion section, by using the chaos theory, and stores the calculated human strange attractor in the index database;
    an attractor evaluation section that gives a quantitative evaluation based on the calculated human strange attractor and the past human strange attractor of the person to be diagnosed or another person to be diagnosed stored in the index database; and
    a display section that displays the evaluation result,
    wherein when the speech signal is an analog speech signal, the speech signal is received by the speech processing section or the analog to digital conversion section, and when the speech signal is a digital speech signal, the digital speech signal is received by the data processing section.

6. A psychosomatic diagnosis system for diagnosing the psychosomatic condition by voice uttered by a person to be diagnosed psychosomatically with respect to questions, comprising:
    an index database in which evaluation results and information for identifying the person to be diagnosed are stored in association with each other;
    a speech processing section that obtains voice of the person to be diagnosed with respect to the questions as a speech signal via a network;
    an analog to digital conversion section that converts the speech signal to a digital speech signal by digitization;
    a data processing section that calculates a human strange attractor from the digital speech signal by using the chaos theory, and stores the calculated human strange attractor in the index database;
    an attractor evaluation section that gives a quantitative evaluation based on the calculated human strange attractor and the past human strange attractor of the person to be diagnosed or another person to be diagnosed stored in the index database; and
    a display section that displays the evaluation result,
    wherein when the speech signal is an analog speech signal, the speech signal is received by the speech processing section or the analog to digital conversion section, and when the speech signal is a digital speech signal, the digital speech signal is received by the data processing section.

7. A psychosomatic diagnosis system for diagnosing the psychosomatic condition by voice uttered by a person to be diagnosed psychosomatically with respect to questions, comprising:
    an index database in which evaluation results and information for identifying the person to be diagnosed are stored in association with each other;
    a processing function distribution section that transmits to a subject's terminal held by the person to be diagnosed a speech processing section for obtaining the voice of the person to be diagnosed as a speech signal, an analog to digital conversion section for converting the speech signal to a digital speech signal by digitization, a questioning section for providing the questions to the person to be diagnosed, a data processing section for calculating a human strange attractor from the digital speech signal by using the chaos theory, and transmitting the calculation result to the psychosomatic diagnosis system, and a display section for receiving and displaying the questions and the evaluation in the attractor evaluation section;
    an attractor evaluation section that stores the human strange attractor calculated on the subject's terminal in the index database and gives a quantitative evaluation based on the calculated human strange attractor and the past human strange attractor of the person to be diagnosed or another person to be diagnosed stored in the index database; and a data reception and distribution section that transmits the questions and the like to the subject's terminal, receives the calculation result from the subject's terminal, and transmits the evaluation result obtained in the attractor evaluation section to the subject's terminal.

8. A psychosomatic diagnosis system according to any one of claims 5 to 7, comprising:

a subject database for storing the information relating to the person to be diagnosed; and a question supply section that supplies at least one question to a diagnosing person, based on the information of the person to be diagnosed, stored in the subject database.

* * * * *